United States Patent [19]

Kensey

[11] Patent Number: 4,589,412

[45] Date of Patent: May 20, 1986

[54] METHOD AND APPARATUS FOR SURGICALLY REMOVING REMOTE DEPOSITS

[75] Inventor: Kenneth R. Kensey, Chicago, Ill.

[73] Assignee: Intravascular Surgical Instruments, Inc., Downingtown, Pa.

[21] Appl. No.: 567,506

[22] Filed: Jan. 3, 1984

[51] Int. Cl.[4] ............................................. A61B 17/32
[52] U.S. Cl. .................................. 128/305; 128/304; 128/305.1; 604/22
[58] Field of Search ...................... 128/304, 305, 305.1, 128/755, 303 R; 604/22

[56] References Cited

U.S. PATENT DOCUMENTS

| 2,937,444 | 5/1960 | Kern | 128/310 X |
|---|---|---|---|
| 3,528,425 | 9/1970 | Banko | 128/305 |
| 3,565,062 | 2/1971 | Kuris | 128/24 |
| 3,659,607 | 5/1972 | Banko | 128/305 |
| 3,732,858 | 5/1973 | Banko | 128/2 B |
| 3,812,855 | 5/1974 | Banko | 128/276 |
| 3,844,272 | 10/1974 | Banko | 128/2 B |
| 3,920,014 | 11/1975 | Banko | 128/230 |
| 3,937,222 | 2/1976 | Banko | 128/305 |
| 3,945,375 | 3/1976 | Banko | 128/6 |
| 3,996,935 | 12/1976 | Banko | 128/276 |
| 4,007,742 | 2/1977 | Banko | 128/230 |
| 4,019,514 | 4/1977 | Banko | 128/230 |
| 4,030,503 | 6/1977 | Clark | 128/304 |
| 4,167,943 | 9/1979 | Banko | 128/305 |
| 4,167,944 | 9/1979 | Banko | 128/305 |
| 4,207,874 | 6/1980 | Choy | 128/6 |
| 4,210,146 | 7/1980 | Banko | 128/305 |
| 4,273,128 | 6/1981 | Lary | 128/305 |
| 4,445,509 | 5/1984 | Auth | 128/305 |

FOREIGN PATENT DOCUMENTS

| 2804015 | 8/1979 | Fed. Rep. of Germany | 128/305 |
|---|---|---|---|
| 605610 | 4/1978 | U.S.S.R. | 128/305 |
| 442795 | 9/1978 | U.S.S.R. | 128/305 |
| 938977 | 7/1982 | U.S.S.R. | 128/305 |

Primary Examiner—Michael H. Thaler
Attorney, Agent, or Firm—Caesar, Rivise, Bernstein & Cohen, Ltd.

[57] ABSTRACT

A procedure and device for use in removing atherosclerotic plaques by inserting a multiple-lumen catheter having a cutting tip into an artery, such as the coronary artery. The cutting tip is rotated by the application of fluid pressure through an inner lumen while, if necessary, negative pressure can be applied through a separate lumen to remove embolic particles as they are cut from the inner wall of the artery. A balloon inflatable through a third lumen may be applied proximally as a protection against possible perforation of the artery.

13 Claims, 10 Drawing Figures

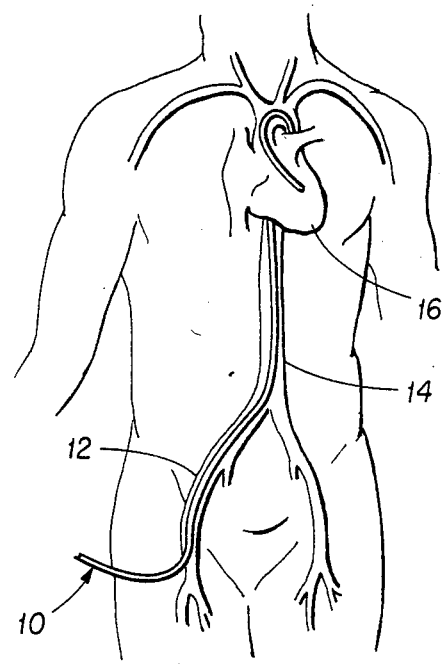
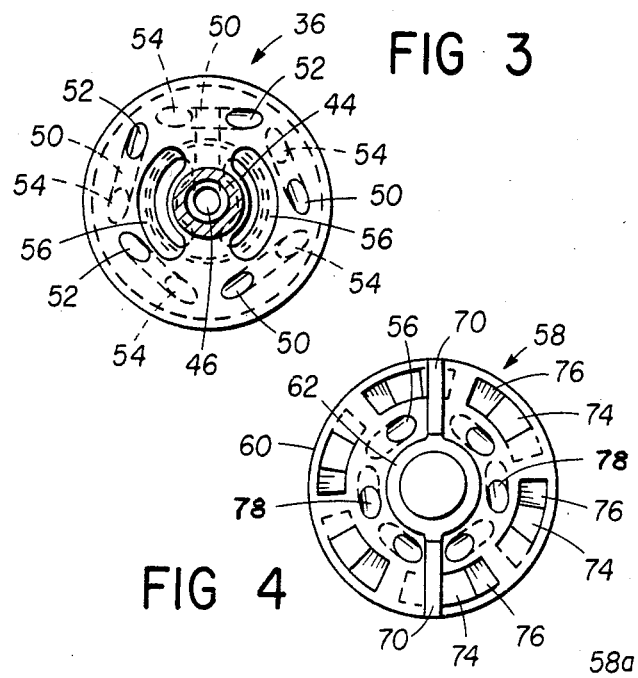
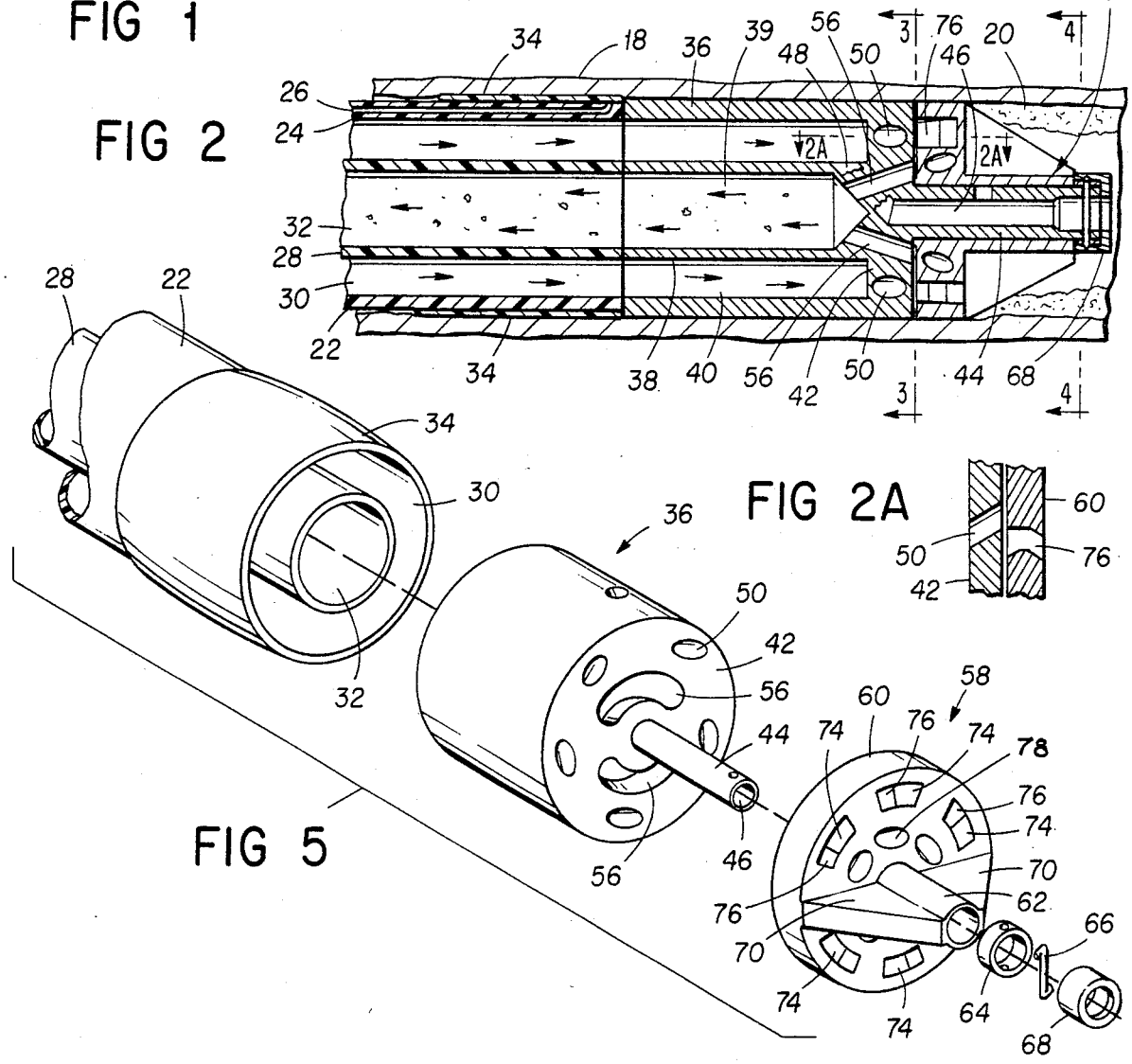

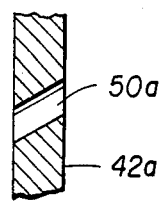
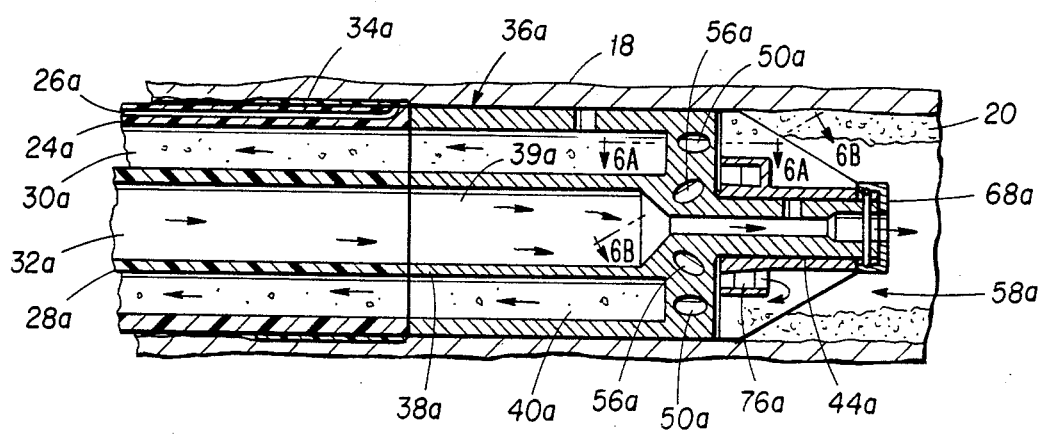
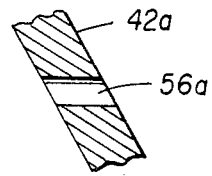
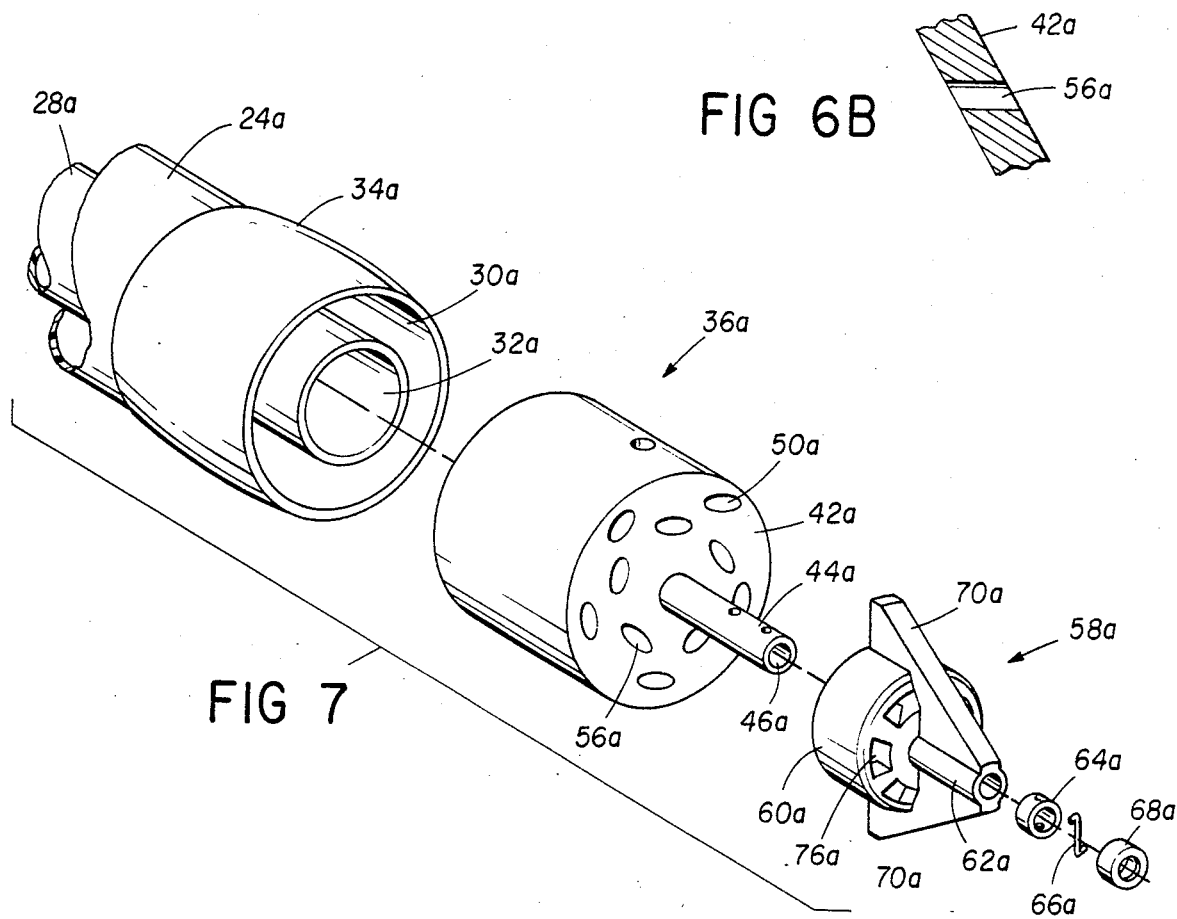

METHOD AND APPARATUS FOR SURGICALLY REMOVING REMOTE DEPOSITS

BACKGROUND OF THE INVENTION

One of the major causes of death in the United States is heart disease produced by atherosclerosis. In atherosclerosis, a plaque forms in the arteries which may involve only a segmental portion of the artery or can involve its entire circumference. This plaque is a "putty-like" or rock-hard material which, if allowed to accumulate, can completely occlude the artery. Also, the plaque can become dislodged from the artery wall and thereby serve as an embolus, or pieces of it may break off and embolize. If complete blockage occurs, and the individual survives, sometimes small new vessels recanalize the area, but the ability of these small vessels to supply any appreciable volume of blood beyond the area of blockage is doubtful.

Coronary athersclerotic narrowing or occlusion has been corrected in recent years most frequently by revascularization of the myocardium. This bypass surgery has become one of the most common surgical procedures performed in the United States. However, the exorbitant cost of myocardial bypass and the associated one to two week morbidity associated with such procedure has led to a procedure termed angioplasty in which an inflatable "balloon" at the end of a catheter is introduced at a selected point in the vascular system and passed into the coronary artery to the site of the occlusion and the plaque compressed by inflating the balloon. Angioplasty, however, is limited in scope of its use because of the variability and the texture of the atherosclerotic plaques and in the inherent limitations of the balloon itself. Moreover, angioplasty is not viewed as a permanent treatment and can result in complications such as artery blow-out, distal emboli spasms, etc.

Development of laser technology for treatment of atherosclerotic plaques is now being conducted, but such a technique, even if successfully developed, has significant limitations.

In a population where average age continues to increase, with a corresponding increase in atherosclerotic heart disease, there is an urgent need for an inexpensive, efficient, safe and effective means for the treatment of atherosclerosis. This urgent need is dictated by the fact that approximately one-fourth of those with atherosclerotic heart disease have as a first symptom sudden death, and each year in the United States alone a million people are diagnosed as having atherosclerotic heart disease. Moreover, a relatively small percentage of those affected with atherosclerotic heart disease are treatable surgically, and there is no indication that there will ever be developed any effective, preventative, pharmacologic treatment of atherosclerotic heart disease.

There is, therefore, a definite and almost urgent need for any technique or device that could produce percutaneous transluminal elimination of atherosclerotic plaques.

SUMMARY OF THE INVENTION

The invention provides a method and a device for removal of atherosclerotic plaques through a relatively simple, safe procedure which can be performed in a short time with limited morbidity. According to the invention, a multiple lumen catheter has a rotating cutter on its distal end. The catheter is introduced at an appropriate site and passed into the diseased artery to the point of the occlusion, the catheter being manipulated under fluoroscopic control similar to the procedure used in balloon angioplasty. One passageway of the catheter provides for the application of controlled fluid pressure, which pressure is utilized to power the cutting tip. The fluid introduced through this lumen can be oxygenated and contain contrast media or other drugs as needed during the procedure. One of the other passageways can be subjected to negative pressure to provide a means of removing the embolic particles as they are cut from the plaque formation in the artery. However, the procedure may emulsify the plaques so that their removal is not necessary. Another passageway may be employed as a protective measure to inflate a proximally located balloon in the event of any complication in which it becomes necessary to stop the blood flow through the artery. Using the technique and device of the invention, the atherosclerotic plaque and any calcium deposits can be quickly and safely cut away resulting in a clean and relatively smooth-wall in the artery.

BRIEF DESCRIPTION OF THE DRAWINGS

FIG. 1 is an illustration of a portion of the human vascular system and showing one possible site for introduction of the device of the invention;

FIG. 2 is a sectional view of an artery and showing the cutting tip and distal end of the catheter located at the site of an atherosclerotic deposit;

FIG. 2A is a sectional view taken on the line 2A—2A of FIG. 2 to show the fluid passageway;

FIG. 3 is an end view of the cutting tip;

FIG. 4 is an end view of the device with the rotatable cutting tip removed;

FIG. 5 is an exploded perspective view of the distal end of the catheter and of the cutting tip;

FIG. 6 is a sectional view similar to FIG. 2 but showing another embodiment of the invention;

FIGS. 6A and 6B are sectional views taken on the lines 6A—6A and 6B—6B of FIG. 6 to show the fluid passageways; and FIG. 7 is an exploded perspective view of the device of the second embodiment.

DESCRIPTION OF THE PREFERRED EMBODIMENTS OF THE INVENTION

In FIG. 1, there is shown a portion of the vascular system of the human body, illustrating one possible application for the method and device of the invention. Referring to FIG. 1, the device of the invention, which is indicated generally by the reference numeral 10, is a flexible catheter that is introduced into the femoral artery 12 at a point in the groin of the patient remote from the site of a blockage that has been determined to exist in a coronary artery, for example. The device 10 is then passed via the aorta 14 into the heart 16 and into the desired coronary artery to the site of the blockage.

In FIG. 2, there is illustrated a coronary artery 18 which contains a partial occlusion or blockage due to a deposit of atherosclerotic plaque 20. FIG. 2 shows the distal end of the device 10 at the site of the blockage caused by the plaque 20. The device 10 consists of a multiple-walled, flexible catheter that has an outer wall 22, and a first inner wall 24 that provides an outer passageway 26 extending throughout the length of the catheter. In addition, the device 10 has an inner tube 28 spaced from the inner wall 24 that provides a relatively large annular passageway 30. Tube 28 also defines a return passageway 32.

The outer passageway 26 terminates in a thin, flexible, annular member 34 the distal end of which is sealed. Thus, fluid pressure introduced into the outer passageway 26 at the proximal end of the device 10 will cause the flexible member 34 to expand or "balloon" throughout its entire circumference. The purpose of this balloon will be described hereinafter.

At the distal end of the device, there is affixed a rigid head 36 which has an inner tube 38 the diameter of which corresponds to the diameter of tube 28. An annular passageway 40 is thus formed in head 36 which passageway 40 is in direct communication with the passageway 30 when the head is affixed to the distal end of the device as shown in FIG. 2. Inner tube 38 also provides a passageway 39 that communicates with return passageway 32 of the catheter. The head 36 is affixed to the distal end of the catheter in any suitable manner so as to provide a fluid tight seal. Head 36 also has a front wall 42 from which extends a hollow shaft 44 that contains passageway 46 extending through the front wall 42 and connects with annular passageway 40 via angular passageway 48.

Front wall 42 of head 36 is relatively thick as shown in FIG. 2, and has formed in it a plurality of passageways 50. As best seen in FIG. 3, each passageway 50 terminates in the outside face of front wall 42 in an oval-shaped opening 52 and in the corresponding opening 54 in the inside face of wall 42, which openings 52 and 54 are offset circumferentially for purpose that will be evident from the description of the rotating cutting head hereinafter. Passageways 50 provide communication from the annular passageway 40 through the front wall 42. In addition, front wall 42 also contains on opposite sides of the shaft 44 somewhat kidney-shaped passageways 56 which provide communication through front wall 42 to the return passageway 39.

Mounted for rotation on shaft 44 is a rotating cutting head indicated generally by the reference numeral 58. Cutting head 58 has a main body portion 60 joined to the tubular portion 62 that engages the shaft 44. The rotating cutting head 58 is retained on the shaft 44 by use of a thrust washer 64 and wire 66 passing through holes in the outer end of shaft 44. A bonnet 68 is then by a press fit slipped over the end of the shaft 44 so as to present a smooth uninterrupted surface on the end of the device.

The rotating cutting head 58 has a pair of cutting blades 70 extending radially outwardly in opposite directions from the tubular portion 62. The cutting surface 72 of these blades converges from the front surface of the main body 60 to the outer end of the tubular portion 62 as best seen in FIG. 5.

The main body 60 of the rotating cutting head 58 also contains a plurality of outer passageways 74 in which are formed angular turbine blades 76. The outer passageways 74 correspond to the spacing of the openings 52 in the head 36, and because of the angularity of passageways 50 fluid flowing through passageways 50 will strike the angular turbine blades 76 so as to impart rotating motion to the cutting head 58.

The cutting head 58 also contains a plurality of angled holes 78 which are angled relative to wall 42. These angled holes 78 capture fluid in an axial pumping fashion and discharge the fluid into passageways 56 in head 36.

The general operation and use of the apparatus of the invention will now be described. After insertion of the apparatus at the appropriate selected site, such as into the femoral artery 12 (FIG. 1), the apparatus is then passed via the aorta 14 into the coronary artery 18 until it reaches the partial occlusion or blockage formed by the deposit of atherosclerotic plaque 20. Introduction of the apparatus can be aided by a fluoroscope, and the contrast medium can be introduced through the passageway 30.

Positive controlled pressure is then applied through the passageway 30 of the catheter which pressure will cause rotation of the cutting head 58 by application of the pressure to the angular turbine blades 76. Simultaneously, the angled holes 78 will induce return flow to the proximal end of the device, acting like an axial flow pump. This flow will pass through kidney ports 56. If necessary, negative pressure can be applied at the proximal end. The return flow will serve to aspirate the particles of plaque being cut away by the rotating cutting head 58, and the pressure differential created by application of positive pressure through the annular passageway 30 will also serve to pull the plaque 20 into a cutting position in the path of the cutting blades 70. During the cutting procedure, positive pressure introduced through the annular passageway 30 will not only serve to drive the rotating cutting head 58, but the fluid infused through this passageway can be oxygenated to eliminate distal ischemia during the procedure. Also, if desired, nitrates, contrast media or any other drugs can be added to the fluid as needed during the procedure. The entire procedure is preferably performed under fluoroscopic control so that the surgeon can determine when the blockage has been completely cut away. Of course, once the blockage has been completely removed to the satisfaction of the surgeon, the apparatus is withdrawn.

Although the apparatus and method of the invention provides minimal risk compared to angioplasty and bypass surgery, it is always possible that an artery wall weakened by disease or containing a congenital defect can break resulting in internal hemorrhage. If this occurs, the flexible member 34 can be inflated through passageway 26 to prevent blood loss until an appropriate surgical procedure can be conducted to correct the break in the arterial wall.

The design of the apparatus of the invention is such that the rigid head 36 and the rotating cutting head 58 are the only rigid portions of the apparatus and these do not interfere with easy passage of the instrument through a tortuous artery. The design of the distal end of the device, and the design of the rotating cutting head alleviates the need for a guiding catheter and may even permit blind application of the device through a tortuous plaque infested artery.

In FIGS. 6 and 7, there are illustrated another embodiment of the invention in which the innermost passageway of the catheter is used for the application of the positive pressure and the exterior annular passageway is used as the return passageway. In this other embodiment, parts corresponding to those of the first embodiment will be referred to by the same reference numeral of the first embodiment but followed by the letter "a". Thus, the catheter has an outer wall 22a and a first inner wall 24a that provides an annular passageway 26a extending throughout the length of the catheter. In addition, the device has an inner tube 28a spaced from the inner wall 24a to define a large annular passageway 30a that in this second embodiment is the return passageway. Tube 28a also defines a center passageway 32a. The outer passageway 26a terminates in a thin, flexible annular member 34a the distal end of which is sealed.

At the distal end of the catheter, there is affixed a rigid head 36a which has an inner tube 38a providing a passageway 40a, that is in direct communication with the passageway 32a. Head 36a has a front wall 42a which contains a plurality of circular passageways 50a that exit the face of front wall 42a at an angle to the surface. These passageways 50a communicate with the return passageway 40a. Front wall 42a of head 36a also contains a plurality of inner passageways 56a. These passageways 56a are in compound angular relationship to the axis of head 36a, having a radially outward direction and a vortex direction. Fluid passing from passageway 39a exits from 56a in a manner such as to impart a spinning action to the fluid and to head 58a. See FIGS. 6 and 7.

A rotating cutting head 58a is mounted on the shaft 44a of head 36a, and has a main body 60a and a tubular portion 62a. A pair of cutting blades 70a diverge rearwardly from the tubular portion 62a. The main body 60a is of a smaller diameter then the diametral position of the passageways 50a so that the passageways 50a communicate directly to the exterior of the device. Because of the angularity of the passageways 56a, positive fluid pressure discharged from these passageways will impinge on the plurality of angled turbine blades 76a causing the cutting head 58a to rotate.

Similar to the first embodiment, the rotating cutting head 58a is held in place on shaft 44a by means of a retaining ring and thrust washer 64a, a retaining wire 66a and a bonnet 68a.

As previously indicated, the apparatus of the second embodiment is used in the same manner as described for the first embodiment. However in this second embodiment, positive fluid pressure is applied through the inner passageway 32a of the catheter which positive pressure serves to drive the rotating cutting head 58a, while return is made through the outer annular passageway 30a. Also, the apparatus of the second embodiment, especially the rotating cutting head 58a, should be simpler and less expensive to manufacture.

Obviously, the particular size and shape of the components of the apparatus as well as the size of the catheter itself will vary according to the application and use of the device. Preferably, the size of the catheter should be kept close to the size of the internal diameter of the artery or other wall in which it is to be inserted in order to assure co-axial movement of the rotating cutting head and limit the amount of the lateral movement of the cutting blades so as to avoid direct contact of them with the arterial wall. Co-axial movement of the apparatus is also aided by the positive pressure applied through the catheter which should aid in directing the rotating cutting head to the center of the artery The design of the device is quite unique in that positive fluid pressure can be used to power the device, and the driving fluid can be used to infuse necessary or desirable drugs during the procedure. Also, the driving fluid can be oxygenated to profuse the distal myocardium thus eliminating time pressure on the surgeon and reducing the likelihood of any technical error. Also, for example, streptokinase can be infused if thrombosis should form in the artery. Nitrates can also be infused for vasodiletation, and calcium blockers may be used to prevent arterial spasm. In contrast to the angioplasty procedure, there is no pressure applied to the arterial walls, thus eliminating many of the complications associated with angioplasty such as blowout, emboli, intimal tearing, etc.

The application of positive and negative pressure necessary during the procedure can be easily accomplished and controlled through known procedures since the triple lumen catheter concept is presently in use in other applications and can be easily adapted when the method and apparatus of the invention is used.

Although the invention is described in connection with certain preferred embodiments and for the particular purpose of removing atherosclerotic plaque, it will, however, be evident to those skilled in the art that the method and apparatus of the invention has application for treatment of conditions other than atherosclerosis. Moreover, the described method and technique for the removal of atherosclerotic tissue is not limited to any particular texture of tissue and is applicable to all atherosclerotic processes. It is further comtemplated that the method and apparatus of the invention will have applications outside of human medicine as well as many applications for treatment of many conditions in the human body. Obviously, the specific size and design of the catheter and cutting tip and the specific design of the rotating cutting blades will depend upon the particular application of the invention. Having thus described the invention, it will be obvious to those skilled in the art that various revisions and modifications can be made to the preferred embodiments described herein without departing from the spirit and scope of the invention. It is my intention, however, that all such revisions and modifications as are obvious to those skilled in the art will be included within the scope of the following claims.

What is claimed is:

1. A method of opening a restriction formed of material inside of a blood vessel, duct, or other lumen within a living being, said method comprising: guiding a flexible catheter, whose outside diameter is close to the inside diameter of the vessel, duct or lumen and having a longitudinal axis and movable working means located at a distal end portion thereof, through the blood vessel, duct, or lumen to the location of the material; applying fluid pressure directly to a portion of said working means to cause said portion to rotate about said axis; and advancing the catheter down said blood vessel, duct, or lumen so that it can flex to conform to the tortuosity of said vessel, duct, or lumen and move into said material while said portion of said working means is rotating to effect the opening of said restriction without appreciable damage to said passageway.

2. The method of claim 1 wherein said working means is a cutting head and including the step of applying suction through the catheter to the area around the cutting head to withdraw particles of material being cut by the cutting head.

3. The method of claim 1 wherein said working means comprises cutter means.

4. The method of claim 3 wherein said fluid pressure is provided to rotate said cutter means via a passage extending through said catheter.

5. The method of claim 1 additionally comprising the step of providing positive pressure to said passageway adjacent the location of said restriction.

6. The method of claim 1 additionally comprising infusing a fluid into said passageway adjacent the location of said restriction.

7. The method of claim 6 wherein said fluid provides the fluid pressure to said working means to cause the movement thereof.

8. The method of claim 6 wherein said fluid is oxygenated.

9. The method of claim 6 wherein said fluid includes a drug.

10. The method of claim 6 wherein said fluid includes a contrast medium.

11. A method of opening a restriction formed of atherosclerotic plaque in a diseased vessel in a living human being, said method comprising: introducing a flexible catheter having a longitudinal axis and a movable cutting head at its distal end rotatable about said longitudinal axis into the diseased vessel at a point remote from the location of the atherosclerotic plaque restriction to be opened; guiding the catheter through the vessel while maintaining blood flow therethrough until the catheter has reached the site of the restriction; applying sufficient fluid pressure through the entire length of said catheter and directly to said cutting head to cause rotation of the cutting head about said longitudinal axis; advancing the catheter down said vessel while the cutting head is rotating to open said restriction; and withdrawing the catheter after the restriction is opened.

12. The method of claim 11 including the step of applying suction at the proximal end of the catheter through the catheter to the area around the cutting head to withdraw particles of plaque being cut by the cutting head.

13. Apparatus for opening a restriction formed of material inside a blood vessel, duct or other lumen within a living being, said apparatus comprising: a catheter whose outside diameter is close to the inside diameter of the vessel, duct or lumen, and which is flexible to conform to the tortuosity of said vessel, duct or lumen and having a distal end portion, a proximal end portion, and a longitudinal axis, fluid-driven, movable cutting means located at the distal end portion, and having a portion rotatable about the longitudinal axis of said catheter and fluid pressure means for continuously directly rotating said portion of said cutting means with respect to said material while said cutting means is advanced down said passageway and into said material to open said restriction, said catheter additionally comprising an inflatable member surrounding its distal end portion proximally from the cutting means, and a passageway coupled thereto to provide for fluid flow from the proximal end portion of said catheter to the inflatable member.

* * * * *